United States Patent
Braga Valente De Almeira Restivo et al.

(10) Patent No.: US 10,856,795 B2
(45) Date of Patent: Dec. 8, 2020

(54) DEVICE FOR MEASURING MUSCLE STRENGTH AND ENERGY

(71) Applicant: UNIVERSIDADE DO PORTO, Oporto (PT)

(72) Inventors: Maria Teresa Braga Valente De Almeira Restivo, Oporto (PT); Manuel Rodrigues Quintas, Oporto (PT); Carlos Manuel De Sousa Moreira Da Silva, Oporto (PT); Tiago Faustino Andrade, Oporto (PT); Bruno Filipe Rodrigues Bento Dos Santos, Oporto (PT)

(73) Assignee: Universidade do Porto, Oporto (PT)

( * ) Notice: Subject to any disclaimer, the term of this patent is extended or adjusted under 35 U.S.C. 154(b) by 272 days.

(21) Appl. No.: 15/759,939

(22) PCT Filed: Sep. 14, 2016

(86) PCT No.: PCT/IB2016/055471
§ 371 (c)(1),
(2) Date: Mar. 14, 2018

(87) PCT Pub. No.: WO2017/046715
PCT Pub. Date: Mar. 23, 2017

(65) Prior Publication Data
US 2018/0249940 A1 Sep. 6, 2018

(30) Foreign Application Priority Data

Sep. 14, 2015 (PT) .......................... 108818

(51) Int. Cl.
*A61B 5/22* (2006.01)
*A61B 5/00* (2006.01)
*A61B 5/11* (2006.01)
*G01L 5/22* (2006.01)
*G01L 1/22* (2006.01)

(52) U.S. Cl.
CPC ............ *A61B 5/224* (2013.01); *A61B 5/1118* (2013.01); *A61B 5/225* (2013.01); *A61B 5/4866* (2013.01); *A61B 5/6825* (2013.01); *G01L 1/2206* (2013.01); *G01L 1/2287* (2013.01);
(Continued)

(58) Field of Classification Search
CPC ....... A61B 5/224; A61B 5/225; A61B 5/6825; A61B 2560/0425; A61B 2562/0252; G01L 1/22; G01L 1/2206; G01L 1/2287; G01L 5/226; G01D 5/02; G01D 5/04
USPC .......... 73/379.01, 379.02, 862.381, 862.621, 73/862.627, 862.634
See application file for complete search history.

(56) References Cited

U.S. PATENT DOCUMENTS 3,922,918 A * 12/1975 Farrar, Jr. ............ A61B 5/1121
73/379.01
4,674,330 A 6/1987 Ellis
(Continued)

*Primary Examiner* — Benjamin R Schmitt
(74) *Attorney, Agent, or Firm* — Leason Ellis LLP

(57) ABSTRACT

A multifunction device for the measurement of the strain on the faces of load cells and displacement on the free ends of load cells allow measurement of the traction and/or compression force and energy expended by a muscle or muscle groups of the human body. Embodiments allow determination of the force profile, the instantaneous power and the average power. Also disclosed is a device for the measurement, recording and digital monitoring of the evolution of force and respective expended energy.

15 Claims, 4 Drawing Sheets

(52) U.S. Cl.
CPC ...... *G01L 5/226* (2013.01); *A61B 2560/0425* (2013.01); *A61B 2562/0252* (2013.01); *G01L 1/22* (2013.01)

(56) References Cited

U.S. PATENT DOCUMENTS

| | | | |
|---|---|---|---|
| 4,866,073 | A | 12/1989 | Dillon |
| 5,125,270 | A | 6/1992 | Kovacevic |
| 5,170,663 | A | 12/1992 | Kovacevic |
| 5,317,916 | A | 6/1994 | Kovacevic |
| 8,601,869 | B2 * | 12/2013 | Miller ................ A61B 5/224 |
| | | | 73/379.02 |
| 2011/0065550 | A1 | 3/2011 | Cohn |
| 2015/0047412 | A1 * | 2/2015 | Hogrel ................ G01L 25/00 |
| | | | 73/1.15 |

* cited by examiner

DEVICE FOR MEASURING MUSCLE STRENGTH AND ENERGY

CROSS-REFERENCE TO RELATED APPLICATIONS

This application is a U.S. National Stage Application under 35 U.S.C. § 371 of International Patent Application No. PCT/IB2016/055471, filed Sep. 14, 2016, which claims priority to Portugal Application No. 108818, filed Sep. 14, 2015, which are hereby incorporated by reference in their respective entireties.

TECHNICAL DOMAIN

The present disclosure refers to a device for the measurement of force (of traction and/or compression) exerted by a given muscle or muscular group of the human body, its temporal evolution, corresponding expended energy and instantaneous and average power.

BACKGROUND

In the state of the art there are several descriptions of devices for measuring muscular forces, namely the documents U.S. Pat. Nos. 4,674,330, 5,125,270, 5,170,663A and 5,317,916.

U.S. Pat. No. 4,674,330 describes a hand grip sensor articulated in one of the ends of its handles, not describing a mechanism capable of robustly measuring the distributed and/or concentrated efforts along said handles.

U.S. Pat. No. 5,125,270 describes a hand grip sensor articulated in one of the ends of its handles, not describing a mechanism capable of robustly measuring the distributed and/or concentrated efforts along said handles.

U.S. Pat. No. 5,170,663A describes a hand grip sensor including a handle centrally placed over two load cells, not describing a mechanism capable of robustly measuring the distributed and/or concentrated efforts along said handles.

U.S. Pat. No. 5,317,916 describes a hand grip sensor with a handle arranged between two posts each equipped with a grip sensor, not describing load cells appropriate for the range of muscular forces in question.

These documents are disclosed in order to illustrate the technical problem addressed by the present disclosure.

GENERAL DESCRIPTION

The present disclosure refers to a multifunction device for the measurement of the strain on the faces of the load cells and displacement on the free ends of the load cells. This way, it is possible to measure the traction and/or compression force and energy expended by a muscle or muscle groups of the human body. The present disclosure allows also to determine the force profile, the instantaneous power and the average power. The present disclosure also relates to a device for the measurement, recording and digital monitoring of the evolution of the force and respective expended energy.

The present disclosure may also be provided with a microcontroller for processing, communicating and storing data, providing a time base. Knowing the force profile during a period of effort and expended energy, it is possible to determine instantaneous power and the average power.

The present disclosure is based on a test body which measures compression and/or traction force, presenting operational ranges adaptable to multiple uses, automatic scales and can be used to measure the force exerted and energy expended by a muscle or different muscle groups, in particular it can be used to measure the force of fingers, legs, arms, thorax, among others.

The load cells of the present disclosure are load cells of the bending type, built-in in one end (in both, at the center) while the other end is free. Therefore, besides the force the displacement on the free end can also be measured every time a load is applied on it. This particular construction of the test body (namely of its load cells) is also adapted to compression and/or traction loads, providing the device with a higher insensitivity to effects of non-uniformly distributed loads, also facilitating its multifunction use.

Generally, the structure of the device now disclosed comprises an elongated main body, a test body and handles or handle-substitute accessories.

The main body is elongated and houses the force measuring system, the longitudinal continuous handle adjustment system or other accessories and the electronic system. Said body is preferentially comprised by a whole piece machined in order to contain in its hollow, and to fix transversally, the test body in its width. The elongated body further comprises longitudinal holes that serve as guidance for the shafts which connect the handles or the accessories to the test body and also incidental recesses and slots for accommodating the electronic system.

The system for measuring the force and expended energy is composed by a test body with a studied geometry, where the sensor elements are accommodated. The force is applied through two shafts that make the connection between the sensorized test body and the handles or accessories used. The structure is designed to ensure a correct force measurement independently of the position where the load is applied on the handles.

The effect of the sensor element being built-in in the central zone causes the shafts, which discharge the load in each of the ends of the test body, to equally deform both the "segments"—in case the load is uniformly distributed, as it is more ordinary (the effects are electrically added). When the load is not uniformly distributed, one of the sides is more deformed, but by electrically adding the effects, the same result is obtained.

The longitudinal continuous adjustment system allows a fine adaptation of the distance between the main body and one of the handles/accessories. The system is composed by two threaded shafts where two pulleys tension a belt or chain which allows performing the longitudinal displacement through the rotation of a third pulley.

The belt may be flat or cogged. The pulleys may be flat or have grooves to increase friction or to fit in a cogged belt.

Alternatively, each of the pulleys may be replaced by a cog wheel. Preferably a chain is then used.

The electronic system that is housed in incidental recesses located in the main body may comprise a module for conditioning and processing the signals from sensor elements, a module for remote communication, a local interface module and a power supply and battery charge module. This way, this device may be conceived to have the capacity to store sufficient data to create a force profile and also store expended energy, instantaneous power and average power and/or to communicate wirelessly with a computer and/or mobile device application and/or human-machine interface.

The possibility to generate a profile of force as a function of time and process data obtaining expended energy, instantaneous power and average power is an advantage of the device hereby described.

The present disclosure of higher functional complexity with evaluation of an enlarged range of physical parameters comprises a reduction of the total weight and dimension in comparison with other similar devices. This disclosure comprises, in particular, dimensions of 114 mm×22 mm×45 mm, approximately. This way, the device now disclosed is a pocket-sized device, portable, smaller, lighter and more ergonomic than known devices and can be used, for example, in clinical settings.

The capacity to provide various parameters, of which force profile, expended energy and average and instantaneous power are highlighted, is equally a technical advantage of the present device.

The measurement of the temporal profile of the force is a more complete and reliable measurement of the user's muscular condition than, for example, the measurement of the maximum force.

The measurements of exerted energy and power, present the user's muscular condition in a more complete and reliable way since they take into account, not only the exerted force, but also energy expended in the exercise of that force.

The present device is portable, in all its different features, has the capacity to measure low hand gripping forces, energy and power with continuous adjustment of the distance between handles, has wireless communication adaptable to different devices such as: personal computers, mobile devices and man-machine interfaces. It also allows the mediation of forces and energy expended by other muscles or muscle groups.

In an embodiment, the device now disclosed may present a set of handles or handle-substitute accessories, depending on the application intended for the device. This set of handles and handle-substitute accessories may be part of the device, making it a multifunctional device.

Throughout the description and claims the word "comprising" and variations of the word, do not intend to exclude other technical characteristics, such as other components, or steps. Additional objects, advantages and characteristics of the invention will become apparent to one skilled in the art upon examination of the description or may be learned through practice of the invention. The following examples and figures are provided by way of illustration, and do not intend to be restrictive of the present invention. Furthermore, the present invention encompasses all possible combinations of particular or preferred embodiments herein described.

A device for measuring muscular strength and/or energy applied on two handles by a user is described, comprising: a first handle; a second handle; two beams built-in as cantilevers from a central support, each constituting a bending load cell; one or more sensors for transducing the strain of each of said beams; two force transmission shafts, wherein one of the ends of each said shaft is rotatably coupled to each of the non-fixed ends of said beams and the other end of each said shaft is coupled to the first handle; wherein said support is jointly coupled to the second handle or wherein said support is the second handle.

In an embodiment, the two built-in beams are formed by a single piece, hereinafter referred to as the test body, which is built-in in said support which thus divides the test body in two parts that constitute said two built-in beams.

An embodiment comprises a hollow elongated body, wherein the two built-in cantilevered beams are arranged longitudinally in the interior hollow of said hollow body, and wherein said hollow body is said support, in particular together with an interlock pin.

An embodiment comprises for jointly coupling said hollow body to the second handle: two threaded shafts, wherein one end of each said shaft is coupled to the second handle; two pulleys with a threaded hole, rotatably coupled to said hollow body and each being threaded into one of the threaded shafts; a belt, cable or chain mounted on said pulleys; such that the rotation of the pulleys synchronized by said belt, cable or chain causes the translation of the second handle relatively to said hollow body.

A rotatable coupling joins two elements together, but allows them to rotate relatively to each other relative to an axis of rotation that is in the coupling itself, as is the case of the coupling of a rotating axis in a fixed support, for example by building-in or by bearings, among other possibilities.

An embodiment comprises a third pulley rotatably coupled to said hollow body and in which said belt, cable or chain is mounted for continuously adjusting the distance between the handle and said body.

In an embodiment, each of the force transmission shafts crosses the hollow body through a hole in the hollow body, with each of the force transmission shafts being guided in its longitudinal movement by that hole.

An embodiment comprises two guide bushings in said holes in the hollow body, each for the guidance of one of said threaded shafts.

In an embodiment, said hollow body is constituted by a single piece.

In an embodiment, said hollow body comprises a main hollow body and an outer shield.

In an embodiment, the fixed ended beams have a hole in order for each to constitute a bending load cell with improved sensitivity in the zone of said hole.

An embodiment comprises two sensors arranged in each of said load cells for measuring the strain corresponding to bending moments, either positive or negative, of the load cells.

In an embodiment, said handles, are either two mobile handles, or one fixed handle and a mobile handle, a fixed handle being a handle suitable for being fixed to or supported by a fixed object or surface, and a mobile handle being a handle suitable for being maneuvered by the user of the device.

In an embodiment, the handles have a straight form, or a wavy form adapted to the human hand, or with circumferences for positioning fingers, or combinations thereof.

In an embodiment, said handles comprise a covering with a straight form, or a wavy form adapted to the human hand, or with circumferences for positioning fingers, or combinations thereof.

In an embodiment, said handles are configured for the device to measure the muscular force and/or energy exerted by the hand, finger, leg, arm, knee, elbow, shoulder, thorax or other muscles of the user of the device.

In an embodiment, said handles are of metal, polymers (for example thermoplastics and elastomers) or combinations thereof.

An embodiment comprises a circuit for collecting and processing of signal from the sensor or sensors, a digital data storage, and a remote communication circuit.

An embodiment additionally comprises a rechargeable power supply circuit.

An embodiment comprises a data processor for collecting and processing data from said sensor or sensors.

An embodiment additionally comprises a non-transient data storage medium comprising computer program instructions for implementing a method of operating a device for measuring muscular strength and energy, computer program instructions which include executable instructions for executing the method of any of the described embodiments.

Additionally described is an operation method of a device for measuring muscular strength and energy applied on two handles of the device by a user, comprising the steps of:—previously calibrating a force-displacement relationship curve between the force exerted on the device handles and the displacement undergone between said handles;—measuring the force applied by the user on the device handles;—calculating the displacement caused between said handles by the force applied by the user through the previously calibrated force-displacement relationship curve;—calculating energy expended by the user on the device handles.

Additionally described is an operation method of a device for measuring muscular strength and energy applied on two handles of the device by a user, comprising the steps of:—previously calibrating a force-displacement relationship curve between the force exerted on the device handles and the displacement undergone at the ends of the beams;—measuring the force applied by the user on the device handles;—calculating the displacement caused at the ends of the beams by the force applied by the user through the previously calibrated force-displacement relationship curve;—calculating energy expended by the user on the device handles.

In an embodiment, the calculation of expended energy comprises adding the energy that is incrementally required to bend the load cell or cells, i.e., the integral of force over displacement.

An embodiment additionally comprises calculating the user's muscular power from the temporal profile of energy expended by the user, particularly the average power or the temporal profile of the user's muscular power.

An embodiment additionally comprises calculating the temporal profile of the force exerted by the user.

BRIEF DESCRIPTION OF THE DRAWINGS

For a better understanding of the present disclosure, the attached figures provide preferred embodiments of the disclosure and should not be seen as limiting the scope of invention.

DETAILED DESCRIPTION

Figure 1:
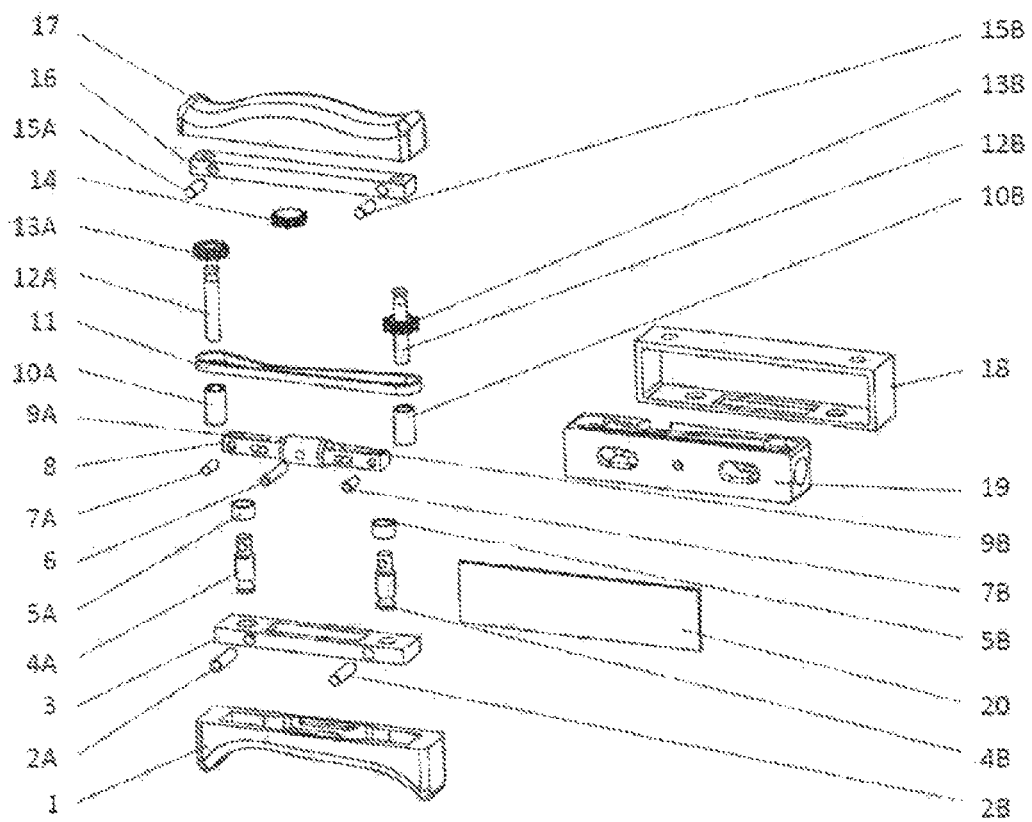
FIG. 1: Representation of an exploded view of the device now disclosed with the main components wherein:
- 1 represents the adaptation covering of the first handle 3;
- 2A and 2B represent pins for locking the force transmission shafts 4A and 4B to the first handle 3;
- 3 represents the first handle;
- 4A and 4B represent force transmission shafts;
- 5A and 5B represent guide bushings of force transmission shafts 4A and 4B;
- 6 represents the interlock pin;
- 7A and 7B represent articulation pins of force transmission shafts 4A and 4B to the test body 8;
- 8 represents the test body;
- 9A and 9B represent electric sensor elements;
- 10A and 10B represent guide bushings of threaded shafts 12A and 12B;
- 11 represents the belt or chain;
- 12A and 12B represent threaded shafts;
- 13A and 13B represent pulleys with threaded hole;
- 14 represents the driving pulley;
- 15A and 15B represent locking pins of the second handle 16 to threaded shafts 12A and 12B;
- 16 represents the second handle;
- 17 represents the adaptation covering of the second handle 16;
- 18 represents the shield;
- 19 represents the body;
- 20 represents the cover of the shield 18.

The exploded view of an embodiment of the device now disclosed (FIG. 1) helps understanding how the several pieces interconnect and originate the different mechanisms comprised by the present disclosure.

In an embodiment, the fixation pins (2A and 2B) fixate the force transmission shafts (4A and 4B) to the first handle (3).

In an embodiment, the articulation pins (7A and 7B) are pins for articulating the force transmission shafts (4A and 4B) to the test body (8).

In an embodiment, the fixation pins (15A and 15B) fixate the second handle (16) to the threaded shafts (12A and 12B).

In an embodiment, the device now disclosed allows directly measuring the force, energy expended during an action of hand gripping as well as the instantaneous power and the average power. However, through the replacement of its handles by accessories, the same device can measure the force, expended energy, instantaneous power and average power of different muscles or muscle groups of the human body, as for example, fingers, legs, arms, thorax, etc., demonstrating in this way its multiplicity of capacities.

In an embodiment, the device comprises a system of continuous adjustment of the distance between handles and a system for measuring force, particularly to traction or compression, and expended energy. The force measuring system can be combined with an electronic system which allows, besides measuring force, to determine expended energy, as well as the average and instantaneous power.

Figure 2:
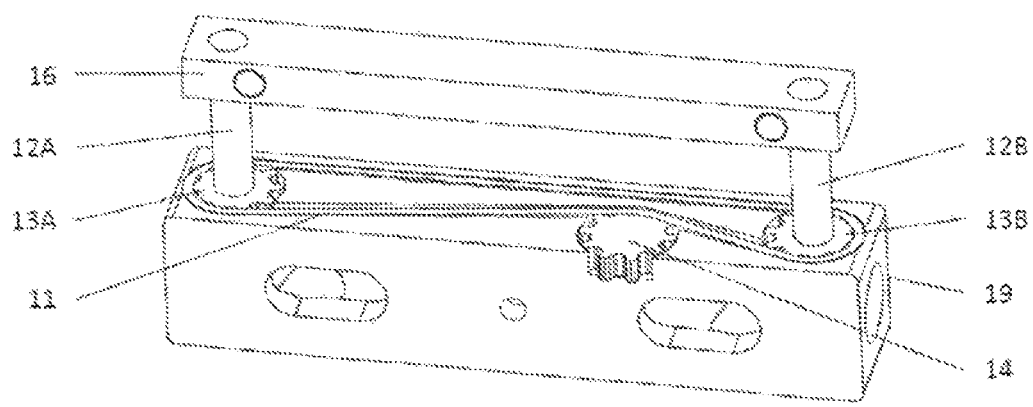
FIG. 2: Representation of the set of constituent elements of the continuous adjustment of the device.

In an embodiment, the continuous adjustment of the distance between handles (3 and 16) is carried out by means of three pulleys (13A, 13B and 14) and a belt or chain (11) (may be a cable). The device user may perform this adjustment through the pulley that is at the surface of the body, in particular the driving pulley (14). The rotation of said pulley promotes the movement of the belt or chain (11) and subsequent rotation of the other two pulleys (13A and 13B). Taking into account that the pulleys (13A and 13B) have a threaded hole for moving in the threaded pins, particularly the threaded shafts (12A and 12B), the synchronous rotation of the pulleys (13A and 13B) promotes the displacement of the second handle. The threaded shafts 12A and 12B are fixed to the second handle (16) through the fixation pins (15A and 15B) which in turn also prevent the rotation of said threaded shafts (12A and 12B). Depending on the direction in which the driving pulley (14) is rotated, the second handle (16) will move away from or closer to the body (19) of the device, carrying out the continuous adjustment to suit the dimension of the hand of the subject under evaluation, in the case of the gripping force measuring function (FIG. 2).

Figure 3:
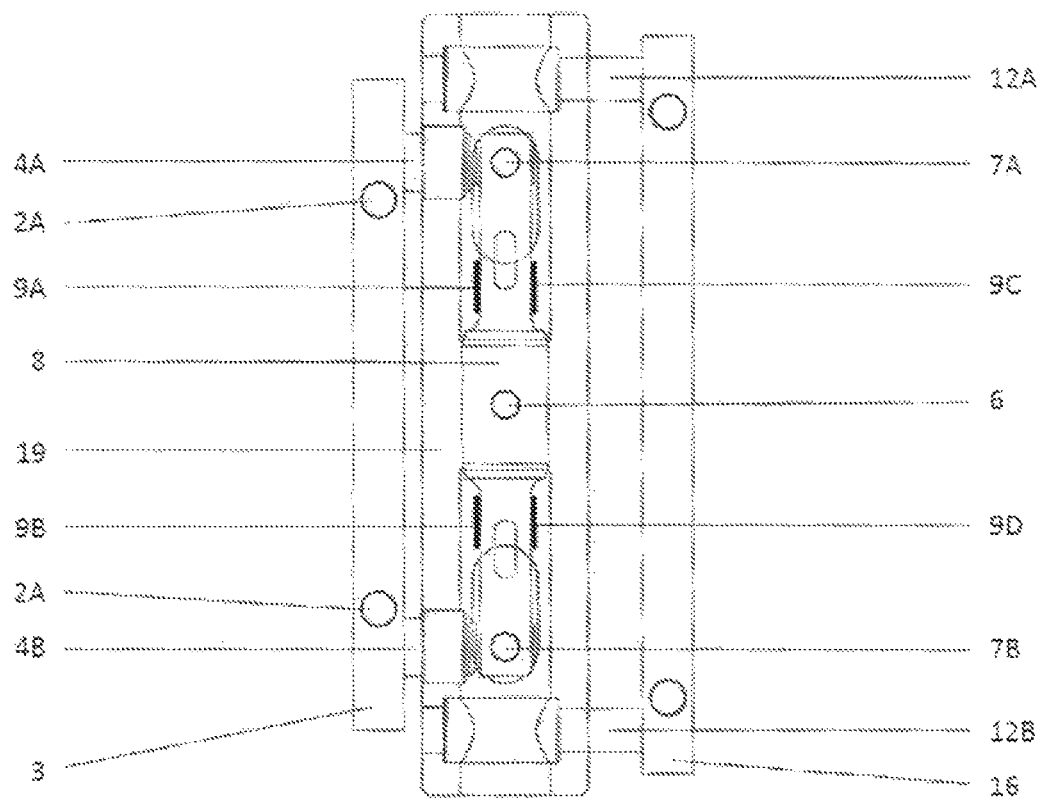
FIG. 3: Representation of the set of constituent elements for the measurement of force and expended energy of the device wherein: 9C and 9C represent electric sensor elements.

In an embodiment, the measurement of the applied force is carried out by the force measuring system (FIG. 3). The force measuring system comprises a test body, particularly the test body (8), fixed to the hollow elongated body (19) by through its own housing in said body (19) and of the interlock pin (6) which crosses the hollow elongated body (19) and the test body in its center of mass.

In an embodiment, the present device also comprises electric sensor elements fixed to the test body (8), in particular four electric sensor elements (9A, 9B, 9C and 9D). The handle 16 is solidarily joined with the body 19 through the threaded shafts 12A and 12B, while the handle 3 is solidarily joined with the ends of the test body 8 by means of the force transmission shafts 4A and 4B. The fastening between the test body 8 and the force transmission shafts 4A and 4B is carried out through the articulation pins (7A and 7B). The fastening between the test body 8 and the handle 3 is carried out through the fixation pins (2A and 2B). The force transmission shafts are guided by means of guide bushings (5A and 5B).

In an embodiment, in the test body 8, two pairs of sensor elements (9A, 9B, 9C and 90D) are symmetrically placed in opposite faces, which allow measuring the strain of the test body (8), in that zone, when a distributed force or load is applied on them. The test body (8) is constituted by two built-in load cells in the center, with the built-in implemented through the hollow elongated body (19) and the interlock pin (6), each load cell being subjected to the relative strain caused by the forces applied in each of its free ends. These ends refer to the zone where the force transmission shafts (4A and 4B) are fixed. This setup guarantees, together with the measurement method of the corresponding strains, reducing the sensitivity of the system to the application of non-uniformly distributed forces or loads.

This mechanic system allied to the electronic solution and after being calibrated, allows the measurement of the traction and/or compression force for any point of application of that force or of a distributed load on the handles (3 and 16) as well as the displacement of the free ends of the test body (8), which will allow determining energy expended in the application of the force which, knowing the time interval of its application, allows determining parameters such as average power and instantaneous power.

Figure 4:
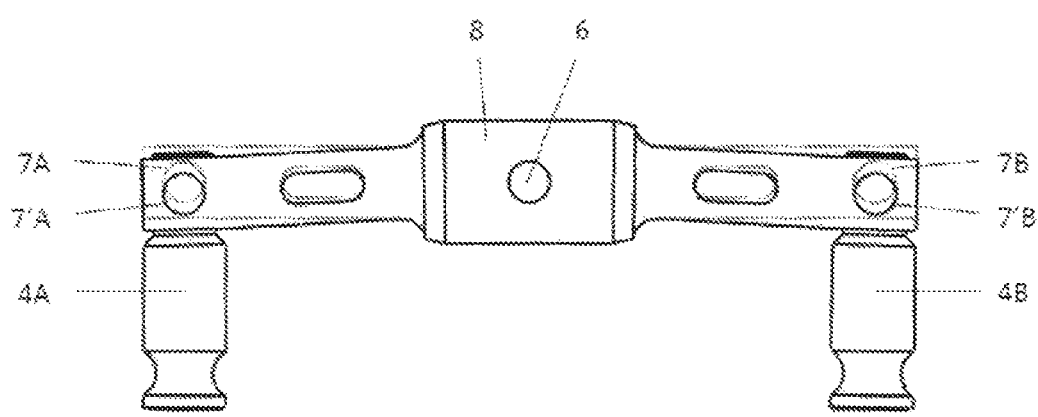
FIG. 4: Schematic representation of the strain undergone by the test body wherein: 7'A and 7'B represent articulation pins of the force transmission shafts 4A and 4B to the test body (8) in the position where a load is being applied.

The measurement of force or load is done through the strain of the test body both to traction and to compression (FIG. 4). The force is applied in the test body (8) through the force transmission shafts (4A and 4B) causing its strain. Said force transmission shafts maintain their vertical direction by virtue of their rotation about the articulation pins (7A and 7B). The interlock pin (6) guarantees the building-in of the test body (8) together with the body (19) of the device.

In FIG. 4, two possible embodiments of the present disclosure are presented. In particular, when no force is exerted, the articulation pins (7A and 7B) are horizontally aligned with the interlock pin (6). However, in a load situation, the articulation pins (7A and 7B) move to a different position, in particular to the positions (7'A and 7'B).

In an embodiment, with the measured values of force and displacement of the free ends of the test body 8, it is possible to obtain expended energy and, associated to a time base that counts the time during the measurement performed by an individual, it is also possible to determine the instantaneous power and the average power and also register the evolution of force over time.

In an embodiment, the handles of the device now disclosed can be adapted with coverings (1 and 17).

Figure 5:
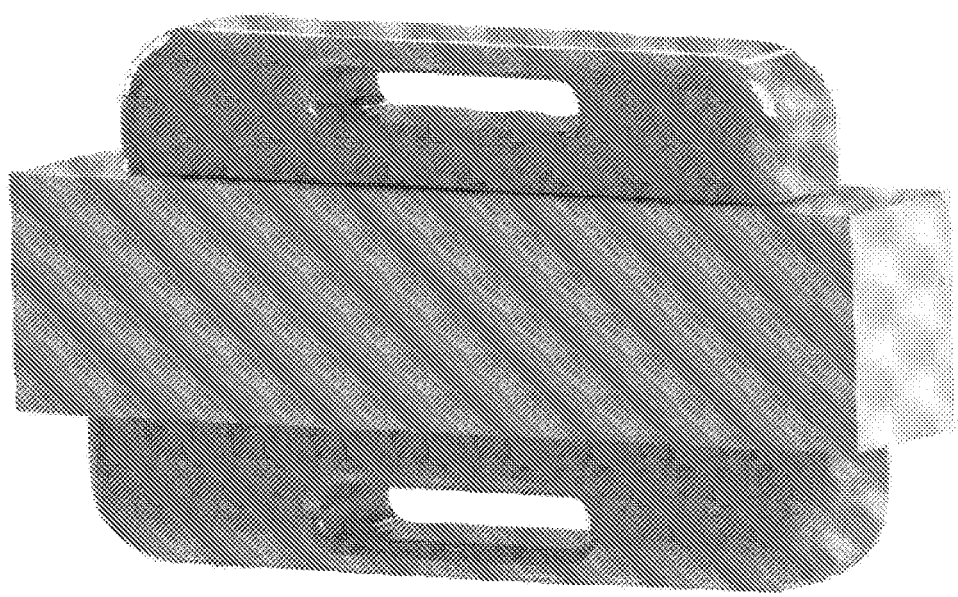
FIG. 5: Representation of a set of handles for the receiving belts for performing measurements of traction and/or of different muscle groups.
Figure 6:
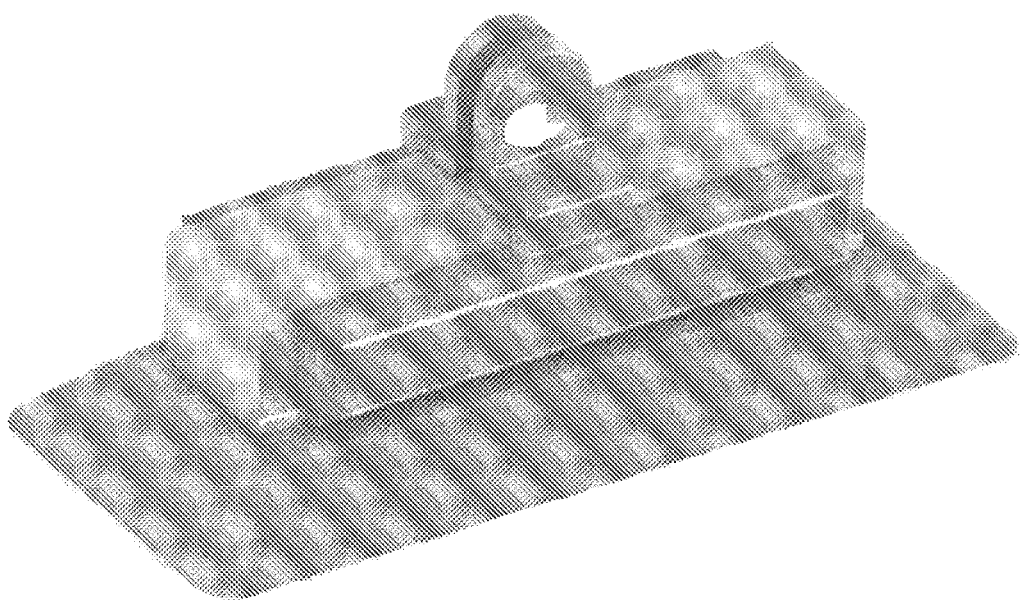
FIG. 6: Representation of a set of handles for the measurement of finger prehension (pinching) force.
Figure 7:
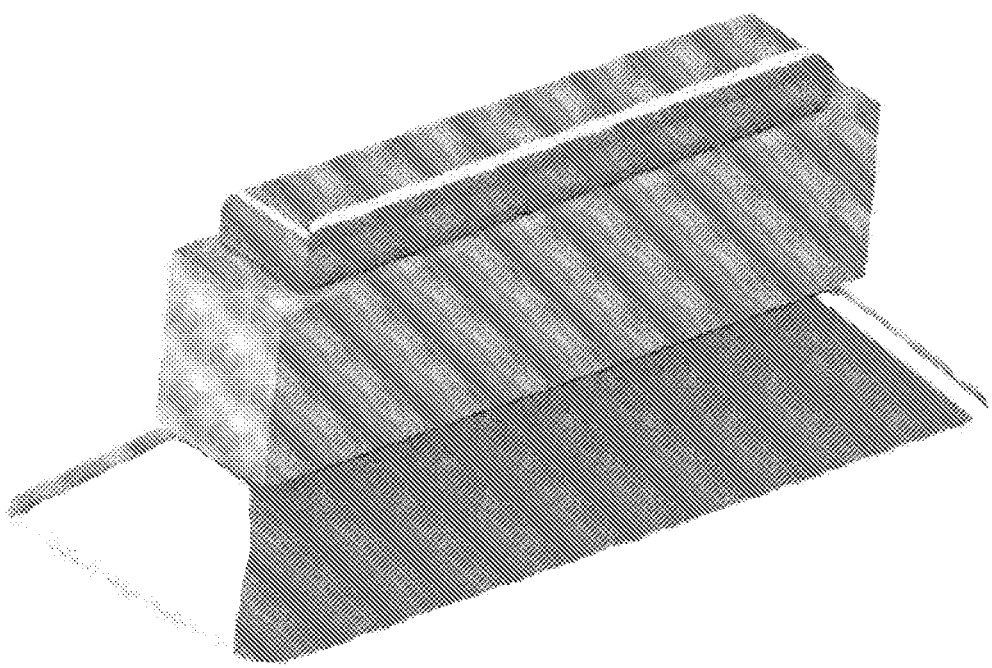
FIG. 7: Representation of a set of handles, in a base format, for application of vertical force, in particular for the measurement of force of biceps and triceps.
Figure 8:
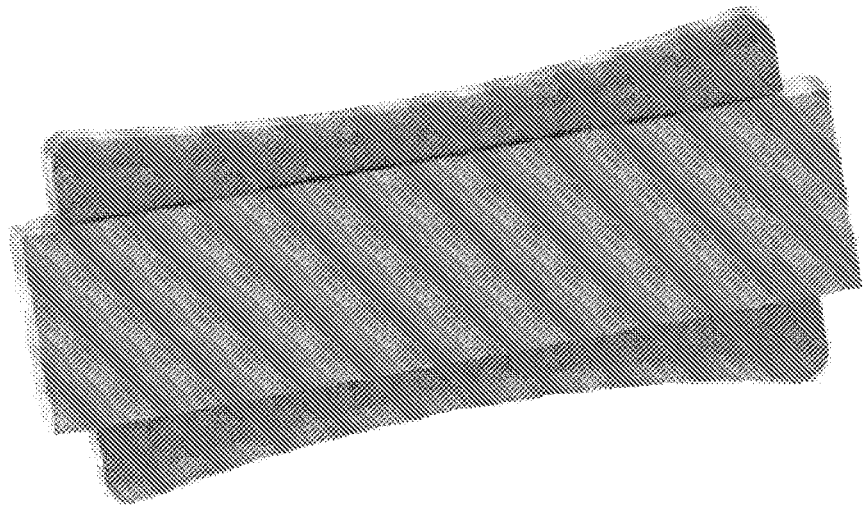
FIG. 8: Representation of a set of handles for the measurement of force between the knees.

In an embodiment, the device now disclosed can be completed with accessories that confer multifunctionality, namely it can be completed with handles that allow the placement of belts for performing measurements of the traction of different muscles or muscle groups namely of the thorax (FIG. 5); handles for measuring the finger "Pinch" gripping force (FIG. 6); handles in a base format for application of vertical force, particularly for measurement of biceps and triceps (FIG. 7); handles for measurement of the force between knees (FIG. 8).

In an embodiment, the device handles may be interchangeable depending of the muscle or muscle group whose strength is to be measured.

When the present disclosure is used as a dynamometer, for measurement of the hand gripping force, it presents continuous adjustment of the distances between handles.

In an embodiment, the device body may be protected, confined and reinforced with the shield and shield cover (18 and 20, respectively). The test body (8) is constituted by two built-in load cells in the center, built-in implemented through the hollow elongated body (19) and the interlock pin (6), each load cell being subjected to the relative strain caused by the forces applied in each of its free ends. These ends refer to the zone where the force transmission shafts (4A and 4B) are fixed.

Even if only particular embodiments of the solution have been represented and described in the present solution, the person skilled in the art will know how to introduce modifications and replace some technical characteristics by other equivalent ones, depending on the requirements of each situation, without departing from the scope of protection defined by the appended claims.

The embodiments presented are combinable. The following claims further define preferred embodiments.

The invention claimed is:

1. A device for measuring muscular force and/or energy applied on two handles by a user, comprising:
   a first handle;
   a second handle;
   two beams built-in as cantilevers from a central support, each constituting a bending load cell;
   one or more sensors for transducing the strain of each of said beams; and
   two force transmission shafts, wherein one of the ends of each said force transmission shaft is rotatably coupled to each of the non-fixed ends of said beams and the other end of each said force transmission shaft is coupled to the first handle;
   wherein said central support is jointly coupled to the second handle or said central support comprises the second handle.

2. The device according to claim 1, wherein the two built-in beams are formed by a single piece, hereafter referred to as a test body, which is built-in in said central support which thus divides the test body in two parts that constitute said two built-in beams.

3. The device according to claim 1, further comprising a hollow elongated body, wherein the two built-in cantilevered beams are arranged longitudinally in the interior hollow of said hollow body, and wherein said hollow body is said central support.

4. The device according to claim 3, further comprising, for jointly coupling said hollow body to the second handle:
- two threaded shafts, wherein one end of each said shaft is coupled to the second handle;
- two pulleys with a threaded hole, rotatably coupled to said hollow body and each being threaded into one of the threaded shafts; and
- a belt, chain or cable mounted on said pulleys;
- such that the rotation of the pulleys synchronized by said belt, chain or cable causes the translation of the second handle relatively to said hollow body.

5. The device according to claim 4, further comprising a third pulley rotatably coupled to said hollow body and in which said belt, chain or cable is mounted for continuously adjusting the distance between the handle and said body.

6. The device according to claim 3, wherein each of the force transmission shafts crosses the hollow body through a hole in the hollow body, with each of the force transmission shafts being guided in its longitudinal movement by that hole.

7. The device according to claim 6, further comprising two guide bushings in said holes in the hollow body, each for the guidance of one of said threaded shafts.

8. The device according to claim 3, wherein said hollow body is constituted by a single piece.

9. The device according to claim 3, wherein said hollow body comprises a main hollow body and an outer shield.

10. The device according to claim 1, further comprising two sensors arranged in each of said load cells for measuring the strain corresponding to bending moments, either positive or negative, of the load cells.

11. The device according to claim 1, wherein said first and second handles are either two mobile handles or are one fixed handle and a mobile handle, a fixed handle being a handle suitable for being fixed to or supported by a fixed object or surface, and a mobile handle being a handle suitable for being maneuvered by the user of the device.

12. The device according to claim 1, wherein the first and second handles have a straight form, a wavy form adapted to the human hand, circumferences for positioning fingers, or a combination of the foregoing.

13. The device according to claim 1, wherein said first and second handles are configured for the device to measure the muscular force and/or energy exerted by the hand, finger, leg, arm, knee, elbow, shoulder or thorax of the user of the device.

14. The device according to claim 1, further comprising a circuit for collecting and processing a signal from the sensor or sensors, a digital data storage, and a remote communication circuit.

15. The device according to claim 1, further comprising a data processor for collecting and processing data from said sensor or sensors.

* * * * *